(12) United States Patent
Kumar et al.

(10) Patent No.: US 8,100,916 B2
(45) Date of Patent: Jan. 24, 2012

(54) INSTRUMENT FOR INSERTING, ADJUSTING AND REMOVING A SURGICAL IMPLANT

(75) Inventors: Rakesh Kumar, Tampa, FL (US); Raymond Murphy, Attleboro, MA (US); Thomas Doherty, Latham, NY (US)

(73) Assignee: DePuy Spine, Inc., Raynham, MA (US)

( * ) Notice: Subject to any disclaimer, the term of this patent is extended or adjusted under 35 U.S.C. 154(b) by 808 days.

(21) Appl. No.: 11/187,178

(22) Filed: Jul. 21, 2005

(65) Prior Publication Data
US 2007/0043378 A1    Feb. 22, 2007

(51) Int. Cl.
*A61F 2/00* (2006.01)

(52) U.S. Cl. .............. 606/104; 606/86 A; 606/916

(58) Field of Classification Search .......... 606/104, 606/99, 286, 287, 288, 289, 291, 914–916, 606/86 A, 250–278; 81/177.2; 403/109.3–109.8
See application file for complete search history.

(56) References Cited

U.S. PATENT DOCUMENTS

| | | | | |
|---|---|---|---|---|
| 1,889,330 A * | 11/1932 | Humes et al. | ........... | 81/453 |
| 2,243,717 A * | 5/1941 | Godoy Moreira | ........... | 606/65 |
| 2,248,054 A * | 7/1941 | Becker | ........... | 81/457 |
| 3,106,233 A * | 10/1963 | Wolny | ........... | 81/53.2 |
| 4,376,397 A * | 3/1983 | Newby et al. | ........... | 81/177.2 |
| 4,440,517 A * | 4/1984 | Potter et al. | ........... | 403/24 |
| 5,649,931 A * | 7/1997 | Bryant et al. | ........... | 606/104 |
| 5,951,554 A * | 9/1999 | Holmes | ........... | 606/104 |
| 6,004,326 A * | 12/1999 | Castro et al. | ........... | 606/99 |
| 6,063,090 A * | 5/2000 | Schlapfer | ........... | 606/270 |
| 6,183,472 B1 * | 2/2001 | Lutz | ........... | 606/86 A |
| 6,258,090 B1 | 7/2001 | Jackson | | |
| 6,398,785 B2 * | 6/2002 | Carchidi et al. | ........... | 606/916 |
| 6,736,820 B2 | 5/2004 | Biedermann et al. | | |
| 6,974,460 B2 | 12/2005 | Carbone et al. | | |
| 7,156,849 B2 * | 1/2007 | Dunbar et al. | ........... | 606/86 A |
| 7,226,453 B2 * | 6/2007 | Chao et al. | ........... | 606/104 |
| 7,491,218 B2 * | 2/2009 | Landry et al. | ........... | 606/246 |
| 2002/0138079 A1 * | 9/2002 | Cohen | ........... | 606/99 |
| 2003/0105471 A1 * | 6/2003 | Schlapfer et al. | ........... | 606/104 |
| 2003/0225408 A1 * | 12/2003 | Nichols et al. | ........... | 606/61 |
| 2004/0020331 A1 * | 2/2004 | Lee | ........... | 81/177.2 |
| 2004/0068269 A1 * | 4/2004 | Bonati et al. | ........... | 606/104 |
| 2004/0102781 A1 * | 5/2004 | Jeon | ........... | 606/73 |
| 2004/0138662 A1 * | 7/2004 | Landry et al. | ........... | 606/61 |
| 2004/0143265 A1 * | 7/2004 | Landry et al. | ........... | 606/61 |
| 2004/0147937 A1 * | 7/2004 | Dunbar et al. | ........... | 606/99 |
| 2004/0243126 A1 | 12/2004 | Carbone et al. | | |
| 2005/0021031 A1 * | 1/2005 | Foley et al. | ........... | 606/61 |
| 2005/0033307 A1 * | 2/2005 | Cook et al. | ........... | 606/104 |
| 2005/0192579 A1 * | 9/2005 | Jackson | ........... | 606/72 |
| 2006/0004378 A1 * | 1/2006 | Raines et al. | ........... | 606/99 |
| 2006/0079909 A1 * | 4/2006 | Runco et al. | ........... | 606/99 |
| 2006/0111712 A1 * | 5/2006 | Jackson | ........... | 606/61 |
| 2007/0129731 A1 * | 6/2007 | Sicvol et al. | ........... | 606/104 |
| 2008/0172062 A1 * | 7/2008 | Donahue et al. | ........... | 606/104 |
| 2008/0243133 A1 * | 10/2008 | Heinz | ........... | 606/104 |

* cited by examiner

*Primary Examiner* — Eduardo C Robert
*Assistant Examiner* — Jan Christopher Merene
(74) *Attorney, Agent, or Firm* — Nelson Mullins Riley & Scarborough LLP

(57) ABSTRACT

An instrument for inserting, adjusting and engaging an implant, such as a polyaxial screw of a spinal fixation system, includes at least one retractable tab for engaging a corresponding recess on the implant and a shaft that moves relative to the retractable tab. The movable shaft selectively moves the tab between an expanded position for engaging the recess and a retracted position out of engagement with the recess. The shaft selectively engages a portion of the implant to rigidify the implant after the retractable tab engages the recess. The axially extending shaft may be disposed within an axially extending passageway of a body assembly. A rotatable collar surrounding the body assembly is coupled to the shaft for moving the shaft relative to the retractable tab.

17 Claims, 16 Drawing Sheets

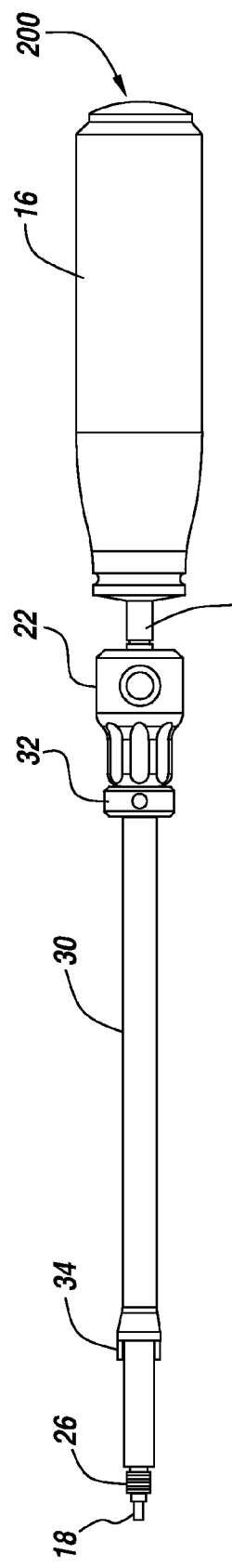
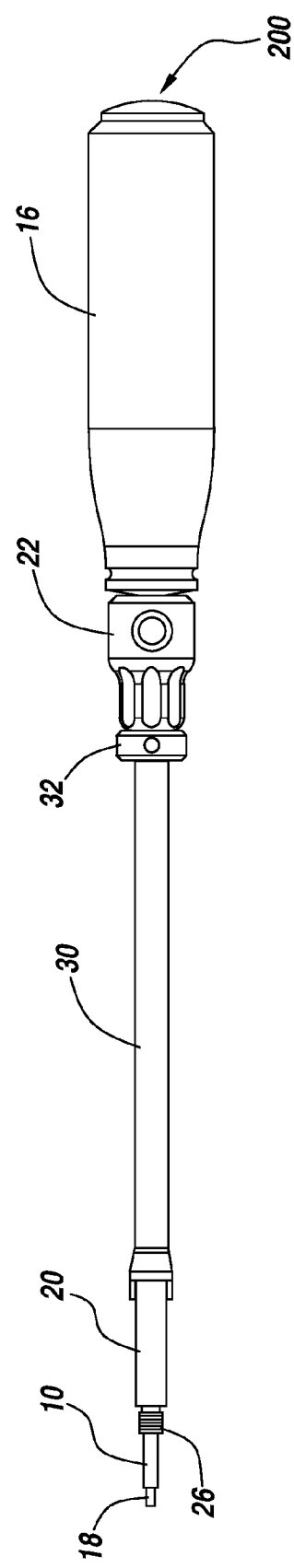
Fig. 2A
Fig. 2B

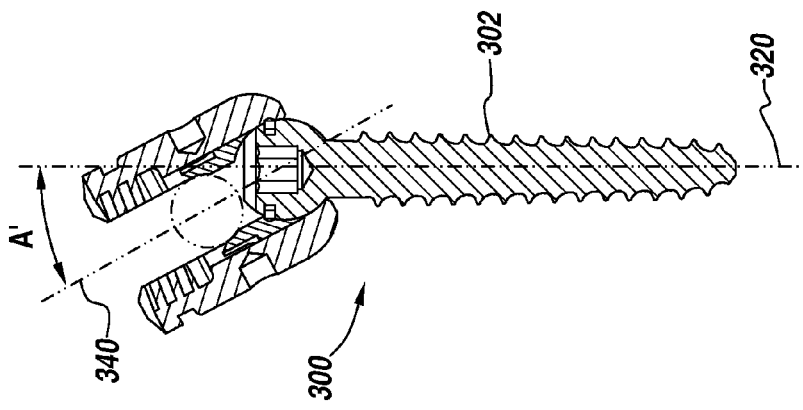
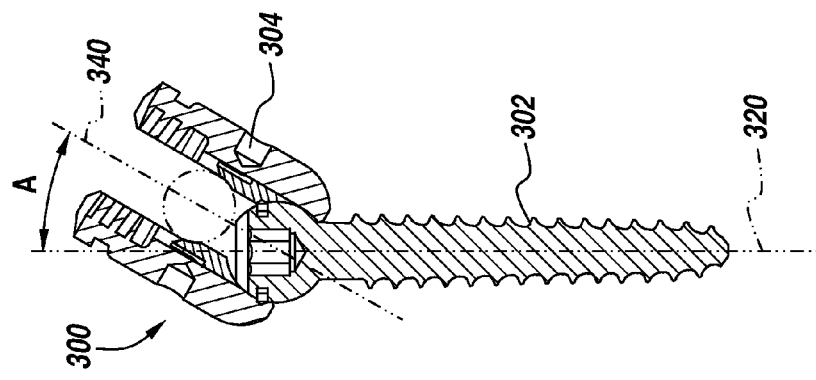
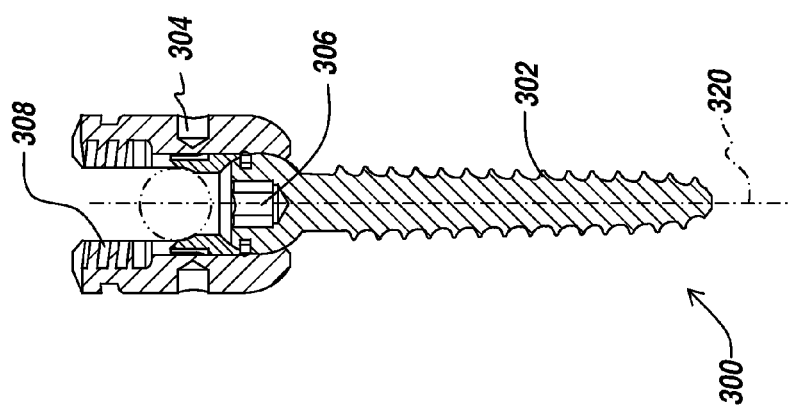

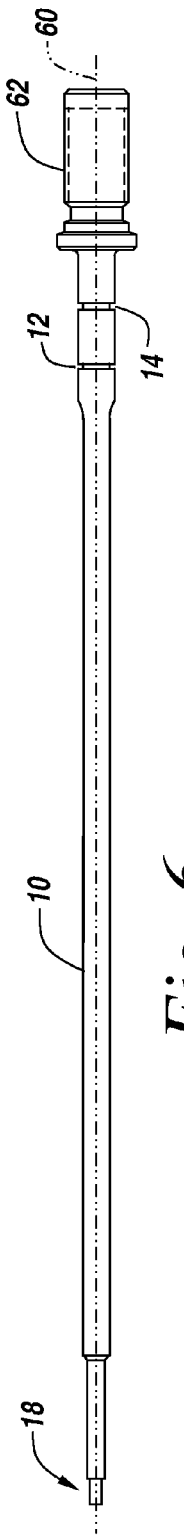
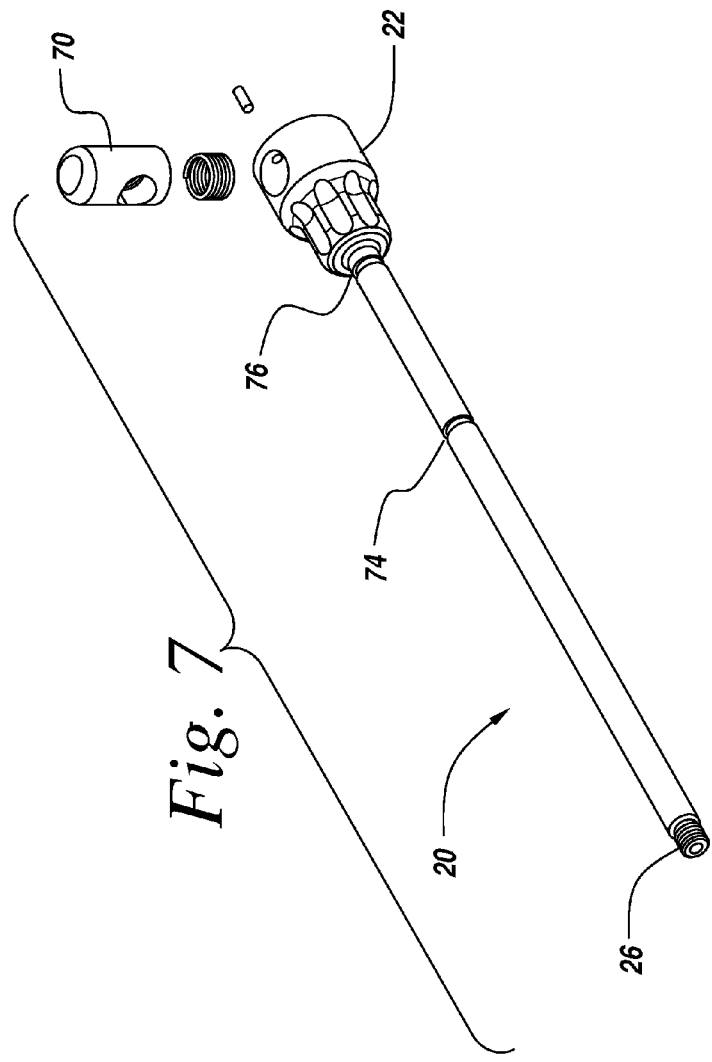
Fig. 6
Fig. 7

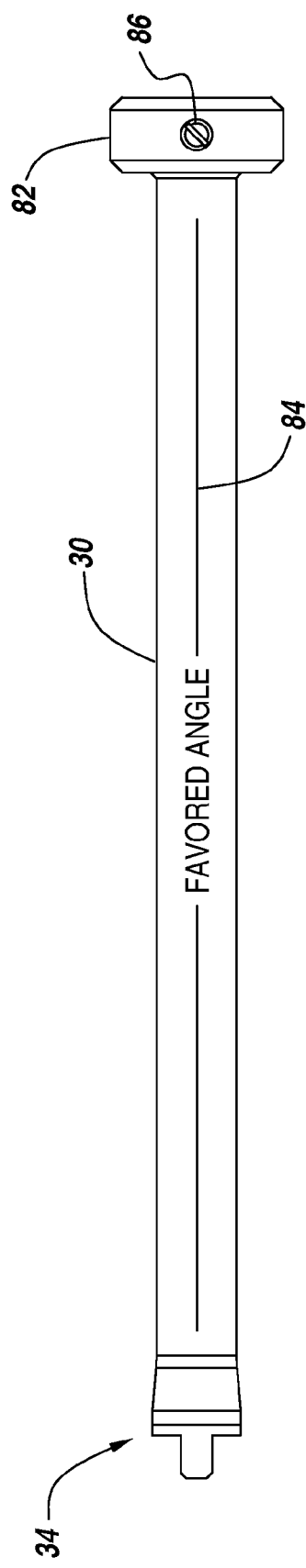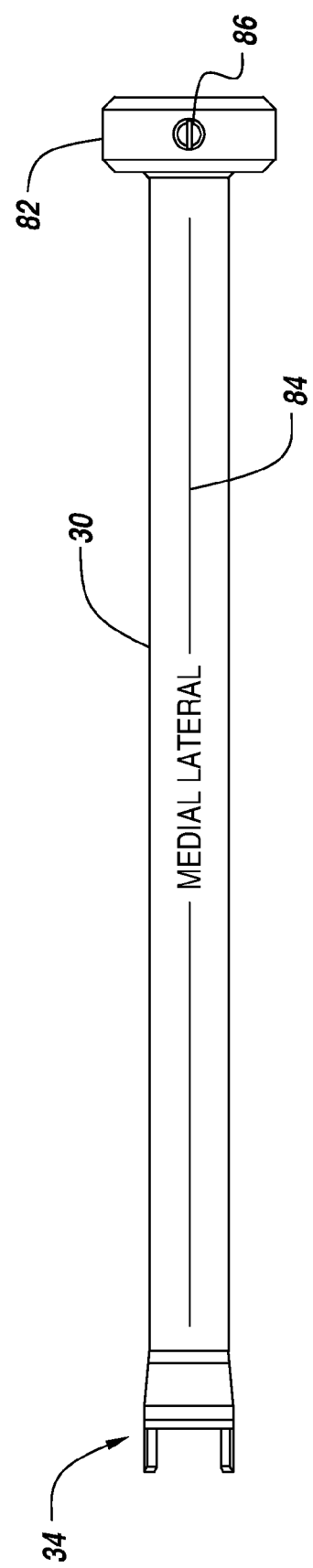

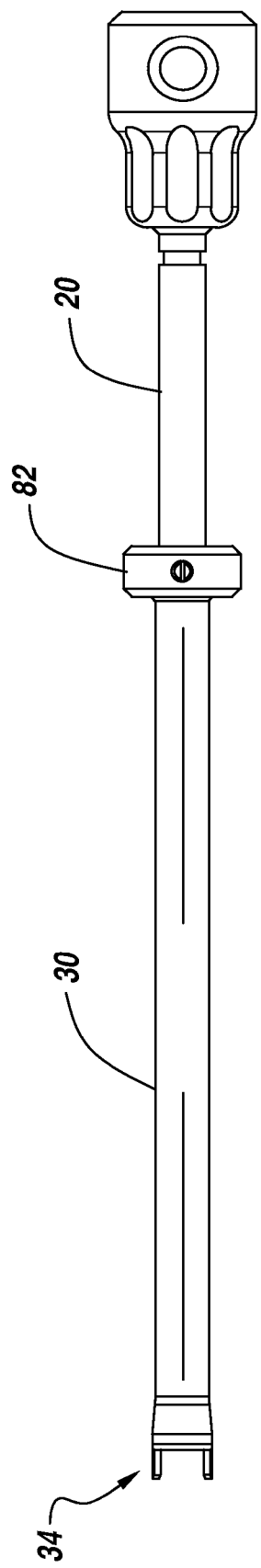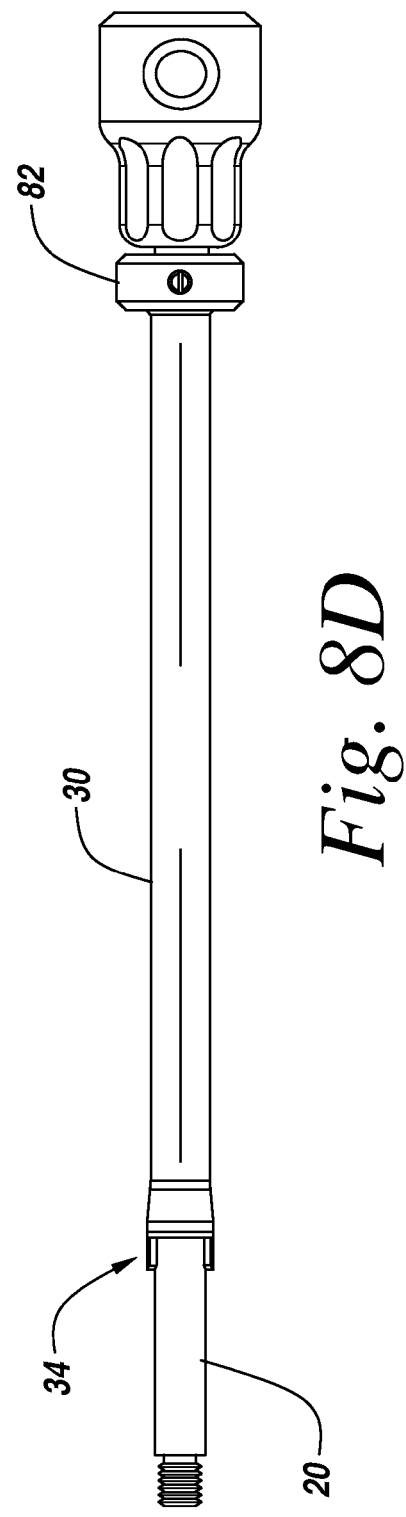
Fig. 8C
Fig. 8D

INSTRUMENT FOR INSERTING, ADJUSTING AND REMOVING A SURGICAL IMPLANT

FIELD OF THE INVENTION

The present invention relates to implantable surgical devices used in surgical procedures. More particularly, the present invention relates to an instrument for inserting, adjusting and removing a spinal implant, such as a polyaxial pedicle screw.

BACKGROUND OF THE INVENTION

Various surgical implants have been used in numerous forms of reconstructive and corrective surgical procedures. One example is a spinal fixation systems used to align, stabilize and/or fix a desired relationship between adjacent vertebral bodies. Such systems typically include a spinal fixation element, such as a relatively rigid fixation rod or plate, that is coupled to adjacent vertebrae by attaching the element to various anchoring devices, such as hooks, bolts, wires or screws. The spinal fixation element may take numerous forms, including a preconfigured shape specific to the implantation site within a patient. Following installation, this spinal fixation element serves to hold the vertebrae in a desired spatial relationship. The spinal fixation element may be implanted for a fixed period of time, to allow healing or fusion to occur. Additionally, the spinal fixation element may be designed for prolonged implantation during the life of a patient.

Each spinal fixation element must be anchored to various regions of a patient. For example various vertebrae sites may be designed by a surgeon as locations for a spinal fixation element. Each of these sites may vary in shape, location, composition and landscape. Therefore, a variety of anchoring devices have been developed to provide for engagement of a particular portion of the bone. Pedicle screw assemblies, for example, have a shape and size that is configured to engage pedicle bone. Such screws typically include a threaded shank that is adapted to be threaded into a vertebra and a head portion. The head portion is typically sized and orientated to allow for a spinal rod to be captured and held in position. This capture of a spinal rod is typically accomplished by providing a U-shaped recess in the head of the pedicle screw which is capable of accepting the spinal rod. Various retention mechanisms, such as a setscrew, plug, or cap, may further be employed to fix the spinal rod in place within the U-shaped recess. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices include hooks and other types of bone screws In many pedicle screws, the head is designed to allow motion in along a plurality of axes relative to the shank of the threaded engagement portion. This freedom of motion of the head thereby aids in alignment and seating of a rod connecting a plurality of screws. Furthermore, the range of motion available may differ based on the direction of head displacement relative to the shank of the pedicle screw. For example, a head may have 30 degrees of motion along a first axis, and only 5 degrees of motion along a second axis. These types of polyaxial screws are generally known as "favored angle" or "biased angle" polyaxial screws.

Polyaxial screws and other implants having movable components are often difficult to manipulate during a surgical procedure, thereby requiring time consuming surgical procedures to properly orient the implant within a patient. Furthermore, surgeons oftentimes must make several attempts at proper implant insertion. To insert and remove the screw, the components of the implant must be made rigid relative to each other, to enable rotation of the shaft in a desired direction by engaging the head. Current drivers for inserting polyaxial screws accomplished this using several techniques, but are generally incapable of inserting a favored angle polyaxial screw in a manner such that the head position is maintained during insertion. Maintaining head position is essential when using a favored angle screw as the range of mobility of the head may be sufficiently small along non favored angle axis such that it may be impossible to use the implanted screw unless the head is orientated properly.

SUMMARY OF THE INVENTION

The present invention provides an instrument for inserting, adjusting and removing an implant in a spinal fixation system, such as a polyaxial pedicle screw with a favored angle position. The instrument includes an engagement mechanism for engaging a first portion of the implantable device and an alignment mechanisms for engaging a second portion of the implantable device. In one embodiment the first portion may be a shank of the polyaxial screw and the second portion may be the head of the polyaxial screw. Following engagement of the alignment mechanism the head and shank are coupled together as a rigid assembly, thereby allowing implantation. Additionally the instrument may contain a counter-rotation mechanism associated with the engagement and alignment mechanisms, such that the counter-rotation mechanism provides for the orientation of the second portion of the implantable device. When used with a pedicle screw having a favored angle, these counter-rotation mechanisms can be utilized in orientating the head (i.e. the second portion of the implantable device) such that the favored angle region is aligned according to a surgeons needs.

According to a first aspect, an instrument for engaging an implant is provided. The instrument comprises an engagement mechanism for selectively engaging a first portion of the implant, an alignment mechanism moveable relative to the engagement mechanism for selectively engaging a second portion of the implantable device and a counter-rotation mechanism moveable relative to the alignment mechanisms wherein the counter-rotation mechanism may be used in orientating the second portion of the implantable device according to a surgeon's needs.

According to another aspect, a driver device for a polyaxial screw comprises an engagement mechanism for engaging the shaft of the polyaxial screw, an alignment mechanism for engaging the head of the polyaxial screw and a counter-rotation mechanism for orientating the head portion of the polyaxial screw is recited. The engagement mechanism defines a first axis and is further sized and orientated for engaging the shaft portion of a polyaxial screw. The engagement of the engagement mechanism with the shaft portion of a polyaxial screw may take numerous forms, including but not limited to the use of a hex shaped driver and recess arrangement. The alignment mechanism of the driver device is additionally orientated along the same axis defined by the engagement mechanism. The alignment mechanism is capable of engaging the head portion of the polyaxial screw such that the head and shaft portions are rigidified relative to each other. The engagement of the head portion of the polyaxial screw may take numerous forms, including the use of a threaded male and female arrangement for rigidifying the head portion of the polyaxial screw. Additionally, a counter-rotation mechanism is orientated along the same axis as the engagement mechanism and the alignment mechanisms such that the counter-rotation mechanism can be used to orientate the head portion of the polyaxial screw relative to the shaft portion of the polyaxial screw by rotating independently of the alignment mechanism and engagement mechanism.

According to another aspect of the invention, a method of implanting a polyaxial screw having a head and shaft portion is further recited. This method includes the steps of engaging the shaft portion of the polyaxial screw with an engagement mechanism, rigidifying the head portion following engagement such that the head portion is maintained in a rigid arrangement relative to the shaft portion and then driving the rigidified head and shaft. The driving of the head and shaft can be in a forward direction, to drive the screw into a patient, or can be in a reverse direction to drive the screw out from a patient. Additionally, the orientation of the head portion of the polyaxial screw can be fixed to a know position following or during the driving of the screw. When used with a favored angle polyaxial screw this fixing of the orientation of the head portion allows for the orientating of the favored angle polyaxial screw in a manner that is most beneficial for the intended operation. Following the driving and fixing of orientation of the head portion of the polyaxial screw each of the engagement mechanism, alignment mechanism and counter-rotation mechanism may be disengaged from the implantable polyaxial screw and removed from a patient.

BRIEF DESCRIPTION OF THE FIGURES

FIG. 2A is a side view of the assembled instrument of FIG. 1 wherein the counter-rotation mechanism is in an extended position.

FIG. 2B is a side view of the assembled instrument of FIG. 1 wherein the counter-rotation mechanism is in a retracted position.

FIG. 3 illustrates a side view of a polyaxial screw suitable for use with the instrument of FIG. 1.

FIG. 3A illustrates a favored angle orientation of a favored angle polyaxial screw.

FIG. 3B illustrates a non favored angle orientation of a favored angle polyaxial screw.

FIG. 6 is a side view of the engagement mechanism for use with the instrument of FIG. 1.

FIG. 7 is a side view of the alignment mechanism for use with the instrument of FIG. 1.

FIG. 8A is a side view of the counter-rotation mechanism for use with the instrument of FIG. 1.

FIG. 8B is a side view of the counter-rotation mechanism for use with the instrument of FIG. 1.

FIG. 8C is an illustration of the assembled instrument wherein the counter-rotation element is in an extended position.

FIG. 8D is an illustration of the assembled instrument wherein the counter-rotation element is in a retracted position.

DETAILED DESCRIPTION OF THE INVENTION

The present invention provides an improved instrument for manipulating an implant, such as a polyaxial screw. The implant may be used in numerous surgical procedures, including spinal fixation surgeries. The instrument of the present invention may be manufactured from a variety of bio-compatible materials, including but not limited to various grades of titanium, stainless steel or plastics. The instrument can be used to straighten, insert, adjust and/or remove an implant without modification or replacement of the instrument. The present invention will be described below relative to an illustrative embodiment directed toward spinal surgery. Those skilled in the art will appreciate that the present invention may be implemented in a number of different applications and embodiments and is not specifically limited in its application to the particular embodiments depicted herein.

Figure 1:
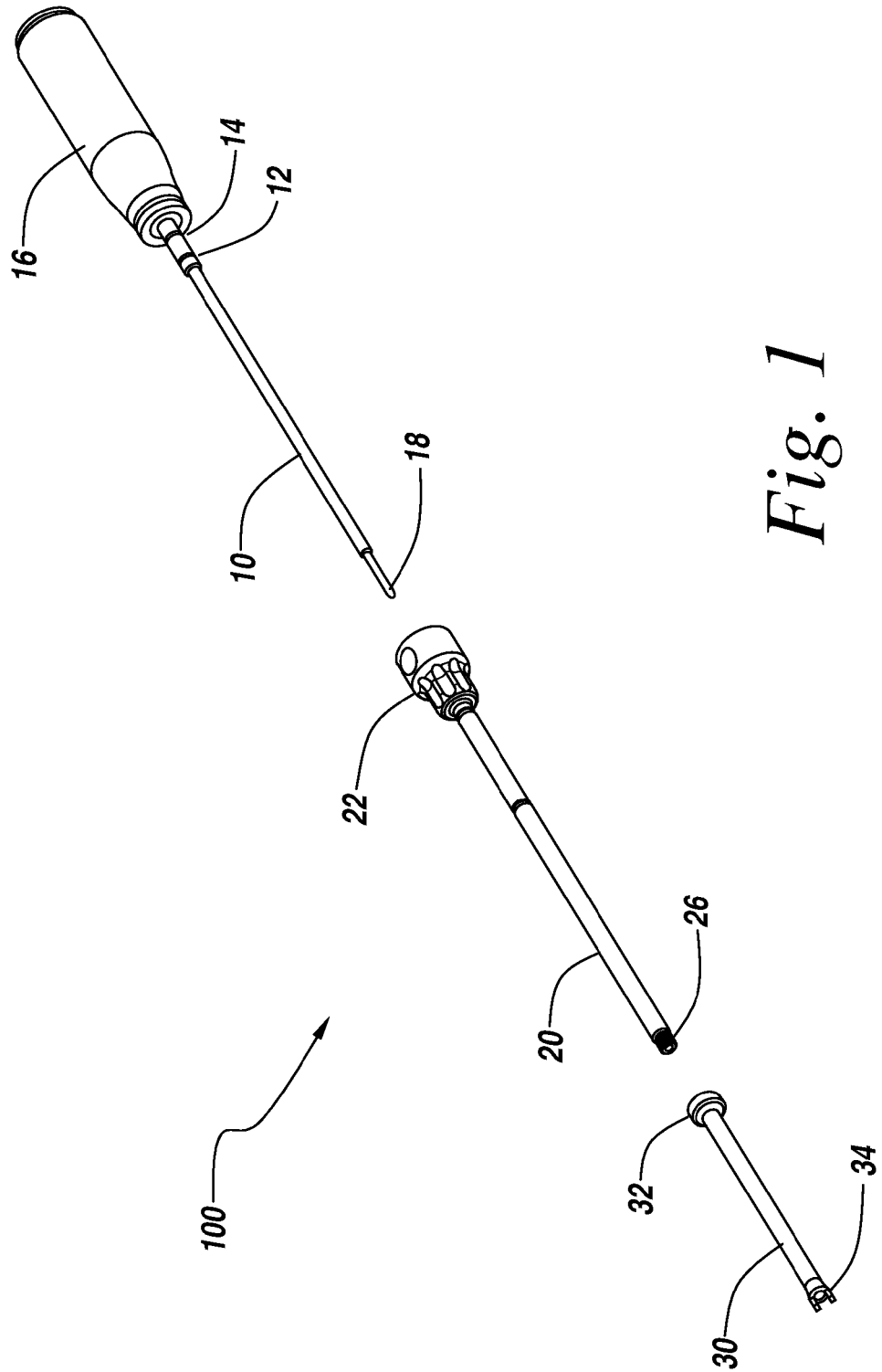
FIG. 1 is an exploded view of an instrument for engaging an orthopedic implant according to an embodiment of the invention.

FIG. 1 illustrates an exploded view of an instrument 100 for engaging an orthopedic implant, such as a favored angle polyaxial screw used in a spinal fixation system, according to an illustrative embodiment of the invention. The instrument 100 can be used with any suitable orthopedic implant, such as monoaxial screw assemblies or hooks and is not limited to use with polyaxial screws per se. In the present embodiment, the instrument 100 is a polyaxial driver device capable of inserting and removing a favored angle polyaxial screw. FIG. 2 is a side view of the assembled instrument 100. The instrument 100 includes a engagement mechanism 10 for engaging a first portion of the orthopedic implant. The engagement mechanism may have a hex tip 18 disposed at its end for use in engaging the first portion of the implant. This first portion of the implant may be the shaft of a favored angle screw. The instrument 100 further includes an alignment mechanism 20 having a tip 26 sized and orientated for coupling with a second portion of the implantable device, such as the head of a favored angle pedicle screw. The alignment mechanism 20 is such that it may slideably move relative to the engagement mechanism 10. A first collar 22 is provided on the alignment mechanism 20 wherein the first collar includes a mechanical stop (not shown) that may prevent linear motion of the alignment mechanism 20 relative to the engagement mechanism 10. This collar 22 may engage first and second circular stop 12,14. These stops 12,14 assist in defining multiple positions of the alignment mechanism when used in the removal and insertion of a polyaxial screw. When the first collar 22 is position over the first stop 12, the alignment mechanism 20 is deemed "extended", while positioning the alignment mechanism over the second stop 14 results in a "retracted" alignment mechanism 20 position. Looking briefly to the assembled view of FIG. 2A, the first collar 22 is orientated to engage a first stop 12 such that the depicted alignment mechanism of the instrument of FIG. 2 is in an extended position. Alternatively, FIG. 2B illustrates the alignment mechanism in a retracted position. While in ether an extended or retracted position, the alignment mechanism 20 remains free to rotate around the axis defined by the engagement mechanism 10. Further associated with the alignment mechanism 20 may be a alignment mechanism coupling element 26. In the illustrated embodiment this coupling element 26 is shown as a threaded fastener capable of engaging a second portion of the implantable device. One skilled in the art will readily recognize that numerous alternative coupling elements 26 may be utilized in practicing the present invention.

A counter-rotation mechanism 30 is further associated with the alignment mechanism 20 and the engagement mechanism 10 of the present invention. The counter-rotation mechanism 30 may slideably move along the alignment mechanism 20 and may simultaneously rotate about the axis defined by the engagement mechanism 10. The counter-rotation mechanism may further include a second collar 32 which provides a readily accessible region for use in rotating and sliding the counter-rotation mechanism 30 along the alignment mechanism 20. The counter-rotation mechanism may further include an anti-rotation finger element 34 disposed along the end of the counter-rotation mechanism 30. This counter-rotation element is sized and orientated to allow engagement with the second portion of the implantable device.

The instrument for operating the implantable device may further include a handle 16 assembly coupled to the engagement mechanism 10 which provides a convenient location for rotating the engagement mechanism 10.

FIG. 3 illustrates a side view of a polyaxial screw suitable for use with the instrument of FIG. 1. This polyaxial screw is solely an illustrative implantable device for use in practicing the present invention and is not intended to be limiting of acceptable implantable devices. In one embodiment the polyaxial screw 300 may be a favored angle polyaxial screw.

The polyaxial screw 300 of the present invention has a first portion, namely a shank 302, and a second portion, namely a head 304. The shank 302, as illustrated herein, may include threads which allow translation of rotary motion into a longitudinal displacement. Associated with the shank 302 is a drive feature 306 for receiving the engagement mechanism 10 of FIGS. 1 and 2. In the illustrated embodiment the drive feature 306 take the form of a female hex arrangement, yet one skilled in the art will readily recognize that the drive feature may be of varying sizes and shaped. For example, the drive feature 306 may be, but is not limited to, a square shape, a triangular shape or a Torx® shape. The tip 18 of the engagement mechanism 10 must be sized and shaped appropriately to engage the drive feature 306 of the illustrated polyaxial screw 300.

Associated with the shank 302 of the polyaxial screw assembly 300 is a head 304. In the present embodiment, the head 304 is allowed to move relative to the shank 302 using a ball and socket arrangement. Using a traditional ball and socket arrangement allows for uniform angular displacement of the head 304 relative to the longitudinal axis of the shank 320. Furthermore, the use of a ball and socket joint between head and shank allows for unimpeded rotary motion of the head 304 relative to the shank 302. In an alternate embodiment, namely a favored angle polyaxial screw, the available angular displacement of the head 304 relative to the longitudinal axis of the shank 320 may be variable.

A favored angle polyaxial screw arrangement is illustrated in FIGS. 3A and 3B. Examples of favored angled screws are disclosed in U.S. Patent Application Publication No. 2002/0058942 and U.S. Patent Application Publication No. U.S. 2003/0055426. In FIG. 3A a first angular displacement "A" is defined as the angular measurement bound by the longitudinal centerline of the shank 320 and the longitudinal centerline of the head 340. As the ball and socket arrangement of the present embodiment allows for angular displacements in numerous directions, a second angular displacement, namely A' may be defined. One such secondary angular displacement is shown in FIG. 3B. Using similar measurement techniques, this second angular measurement A' is again the maximum displacement defined by the longitudinal centerline of the shank 320 and the head 340. In the present case the angular displacement of A' is clearly less than that of A. In lieu of this, the angular displacement associated with the orientation of FIG. 3A is deemed the favored angle.

The use of favored angle polyaxial screws allows a surgeon to implant a polyaxial screw designed for a specific range of angular displacement based upon treatment requirements. As the favored angle feature is only applicable to a specific direction and only covers a small range of potential head 304 locations it is essentially to properly orientate the polyaxial screw 304 such that the favored angle feature is appropriately situated. Orientation of the head 304 appropriately is accomplished using the counter-rotation mechanism 30 illustrated in FIGS. 1 and 2. During insertion of the screw into bone the surface of the bone is typically uneven. With polyaxial screws the head 304 may start to angulate relative to the shank 302 once the head contacts the surface of the bone. This can cause the hex tip of the screwdriver to become lodged in polyaxial screw assembly making it difficult to remove screwdriver from the screw.

Figure 4:
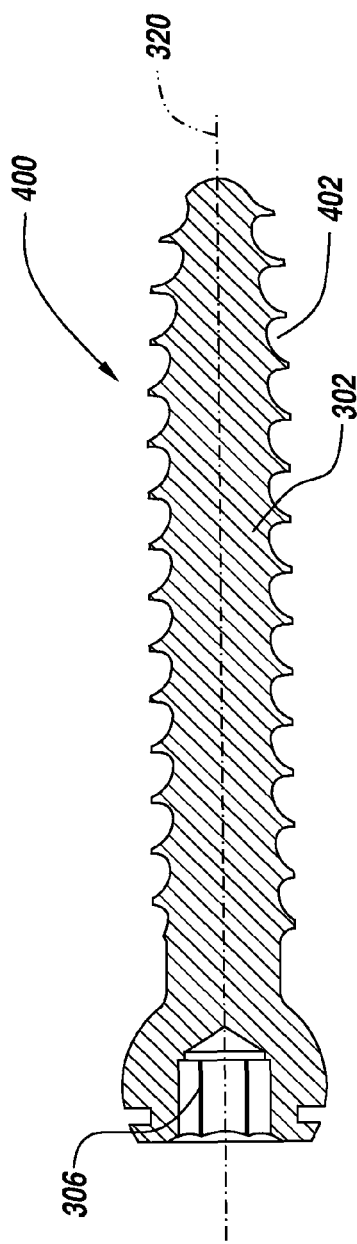
FIG. 4 is a detailed view of the shank portion of the polyaxial screw of FIG. 3.

FIG. 4 is a cutaway illustration of the shank 302 portion of a polyaxial screw assembly 400. In this illustration the drive feature 306 is readily apparent. The illustrated to drive feature 306 is depicted as a female hex arrangement, yet one skilled in the art will readily recognize that the hex 306 may take numerous shapes such as a triangular shape, square shape or Torx® shape. The drive feature 306 must be sized for coupling with an applicable male tip 18 (not shown) of the engagement mechanism 10 of FIG. 1 and FIG. 2. A longitudinal axis 320 is further defined as passing through the centerline of the shank portion of the polyaxial screw. Additionally, the shank 302 may have an exterior screw thread arrangement 402 such that rotation of the shank using the drive feature 306 results in motion along the longitudinal axis 320. One skilled in the art will recognize that the screw thread arrangement 402 of the shank 302 may be of a fixed or variable pitch, or some combination thereof. Furthermore the screw arrangement 402 may cover the entirety of the shank 302, a portion of the shank 302 or any combination thereof.

Figure 5:
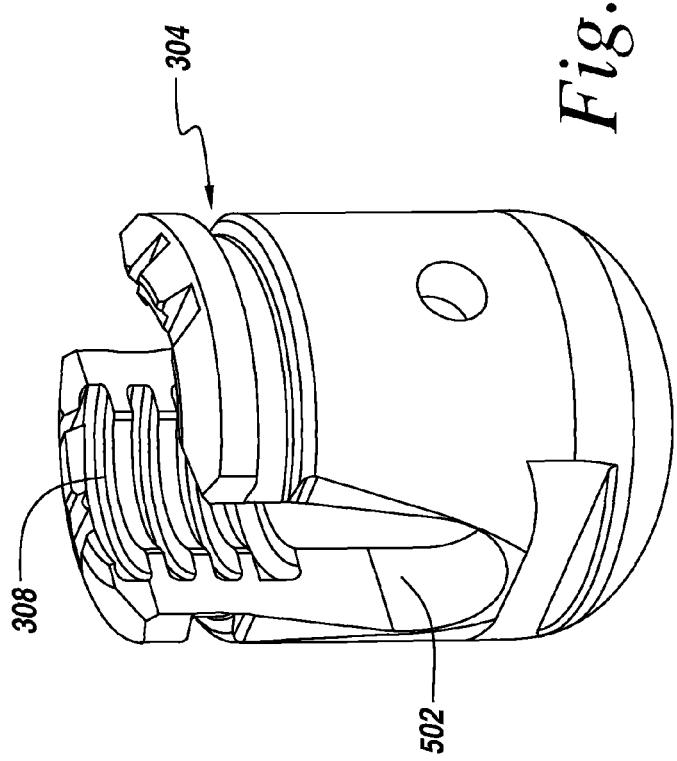
FIG. 5 is a detailed view of the head portion of the polyaxial screw of FIG. 3.

FIG. 5 is a isometric view of the head portion 304 of a polyaxial screw. In the illustrated embodiment the head portion 304 includes a U-shaped recess 502 disposed along opposing sides of the head 304. This U-shaped recess 502 serves numerous functions. Firstly additional implantable devices may be disposed within the recess defined by the U-shaped recess 502. For example, during spinal surgery a spinal surgical rod may be disposed across the opposing U-shaped recess 502. Following insertion of the spinal rod, a screw (not shown) may be threaded into the threaded setscrew recess 308 for use in retaining the spinal rod. Additionally, the U-shaped recess 502 allows for the insertion of the anti-rotation element 34, disposed at the end of the anti-rotation mechanism 30, into the head 304 of the polyaxial screw.

During insertion or removal of the polyaxial screw into a patient the anti-rotation mechanism 30 allows for proper orientation of head position using the opposing U-shaped recesses 502 of the head 304.

FIG. 6 is a side view of the engagement mechanism 10 for use with the instrument of FIG. 1. The engagement mechanism includes a hex tip 18 for coupling with a drive feature 306 disposed on the shank of a polyaxial screw (not shown) The engagement mechanism further includes a first and second stop 12,14 disposed within the engagement mechanism 10. In the present embodiment these stops 12, 14 are illustrated as circumferential grooves within the engagement mechanism 10. One skilled in the art will readily recognize that the stops 12 14 may take numerous alternative forms such as protruding circumferential regions. Additionally, an engagement mechanism tang 62 is illustrated. This tang 62 may be used to couple the engagement mechanism 10 to an appropriate handle which may be used by a surgeon to provide rotary motion to the engagement mechanism 10. Rotation of the engagement mechanism 10 thereby occurs along the central axis of the engagement mechanism 60.

FIG. 7 illustrates the alignment mechanism 20 as illustrated in the exploded view of FIG. 1. The alignment mechanism 20 is oriented to surround the engagement mechanism and is capable of moving both longitudinally and rotationally along the central axis of the engagement mechanism 60. The alignment mechanism 20 may include a coupling mechanism 26 sized for coupling to the setscrew recess 308 of the polyaxial screw head 304. Coupling of the alignment mechanism 20 coupling mechanism 26 to the setscrew recess 308 may occur after insertion of the engagement mechanism 10 into the drive feature 306 of the shank of the polyaxial screw. In use during a surgical procedure, the engagement mechanisms is first deployed such that the drive feature 306 of the shank 302 of the polyaxial screw is properly engaged by the hex tip 18 of the engagement mechanism. During insertion of the engagement mechanism 10 to engage the drive feature 306 of the shank of the polyaxial screw 302 the alignment mechanism 20 is oriented in a retracted position wherein the first collar 22 engages a second stop position 14 of the engagement mechanism. Upon engagement of the engagement mechanism with the drive feature 306 of the shank 302 of the polyaxial screw, the first collar 22 may be moved to engage a first stop position 12. Engagement of this first stop may occur following depression of a spring loaded release button 70 associated with the first collar 22 such that the first collar 22 is initially disengaged from the second stop 14 and is capable of moving to a first stop 12 position. The orientation of the first collar 22 over the first stop position is herein refereed to as an "engaged position" of the alignment mechanism. In contrast, the location of the first collar 22 over the second stop 14 is herein referred to as a "retracted position" of the alignment mechanism 20.

Following the positioning of the alignment mechanism 20 into a engaged position, the fist collar 22 is manipulated to couple the alignment mechanism 20 with the head 304 of the polyaxial screw. In the illustrated embodiment a threaded coupling mechanism 26 is illustrated for coupling with the setscrew recess 308 of the head 304. One skilled in the art will readily recognize alternative coupling mechanisms such as a helical dovetail may be employed in keeping with the present invention. The coupling of the alignment mechanism 20 with the head of the polyaxial screw 304 is accomplished by rotating the first collar 22 to engage the threads of the coupling element 26 with the threads of the setscrew recess 308.

Upon coupling of the head of the polyaxial screw 304 with the alignment mechanism 20 a rigid polyaxial screw assembly, comprising a head 304 and shank 302, is formed. The coupled alignment mechanism 20 and polyaxial screw head 304 is such that angular displacement away from the longitudinal axis of the screw 320 is no longer possible. In such an arrangement a surgeon may drive both polyaxial screw shank 302 and head 304 as a single unit into a patient using a handle 16 disposed upon the end of the engagement mechanism 10. Such a rigidified head 304 and shank 302 assembly prevents unintended loss of engagement of the hex tip 18 with the drive feature 306 of the shank. Furthermore, as the polyaxial screw is rigidly affixed to the surgical instrument of the present invention, unintended loss of the polyaxial screw within a body cavity is prevented. As a surgeon is often times working in a view impaired setting, loss of a polyaxial screw assembly may result in difficulties in relocating the screw as well as relocating the drive feature 306 for further driving of the screw. Additionally, unintended contact of the head 304 with the surgical site is prevented, as compared to existing polyaxial screw devices which allow the head 304 to move freely during insertion of the polyaxial screw. It is equally important that the screwdriver can be unthreaded from the polyaxial screw. In the event that the screwdriver tip becomes lodged in the screw the mechanical advantage of threads in the head of the polyaxial screw to remove the driver from the screw.

Further disposed along the length of the alignment mechanism 20 is a third and fourth stop 74, 76 for use in conjunction with the counter-rotation mechanism. As illustrated in FIGS. 8A and 8B, the anti-rotation element 30 includes a second collar 82 as well as a anti-rotation finger element 34. The second collar 82 may include a spring loaded setscrew 86 designed for engaging the third or forth stop of the alignment mechanism 20 as required by a surgeon during use. When the spring loaded setscrew 86 engages the fourth stop 76 the counter-rotation mechanism is deemed to be in a "retracted" position. In contract, the engagement of the spring loaded setscrew 86 with the third stop 74 the counter-rotation mechanism is considered to be in a "extended" position. FIGS. 8C and 8D illustrate the anti-rotation mechanism of the assembled instrument in an extended and retracted position respectively. As understood by one skilled in the art, the engagement of the counter-rotation mechanism in a retracted and extended position may be accomplished using a variety of suitable techniques beyond the spring loaded setscrew depicted in the present embodiment such as employing a bal-seal or spring loaded button. The use of the depicted arrangement, therefore, is not intended to be limiting of the scope of the present invention.

Upon selecting an engaged position for counter-rotation mechanism 30, a surgeon may manipulate the second collar 82 to allow the engageable protraction 34 to mate with the U-shaped recess 502 of the head 304 of the polyaxial screw.

Additionally associated with the counter-rotation element 30 is an indicating mechanism capable of informing a user of the orientation of the head of the polyaxial screw during a surgical procedure. As depicted in FIG. 8A for example, the indicating mechanism 84, which corresponds to a known position of the engageable protrusion, informs a surgeon that the favored angle position is orientated along the axis noted by the indicating mechanism 84. This is achieved by utilizing a favored angle screw wherein the underside of the head includes a slanted region which provides a region wherein additional range of motion of the head relative to the shank is provided. In view of this, an indicating mechanism 84 may be aligned with this slanted underside region of the favored angle screw when the screw is attached to the driver. In contrast, as illustrated in FIG. 8B, a second indicating mechanism, which corresponds to a different engageable protrusion 34 orientation, denotes that a secondary orientation of the head 304 of the polyaxial screw 300 has been achieved.

During a surgical procedure, a surgeon may use the counter-rotation mechanism to selectively oriented the head of the polyaxial screw in an appropriate position such that the favored angle arrangement can be exploited for use in a surgical procedure. Additionally When using a non favored angle polyaxial screw the indicating mechanism 84 86 may be utilized in selectively orientating the head 304 of a polyaxial screw 300 such that subsequent surgical procedures, such as insertion of spinal bars, is readily accomplished due to the proper orientation of the u-shaped slots within the head 304 of the polyaxial screw 300.

Figure 9:
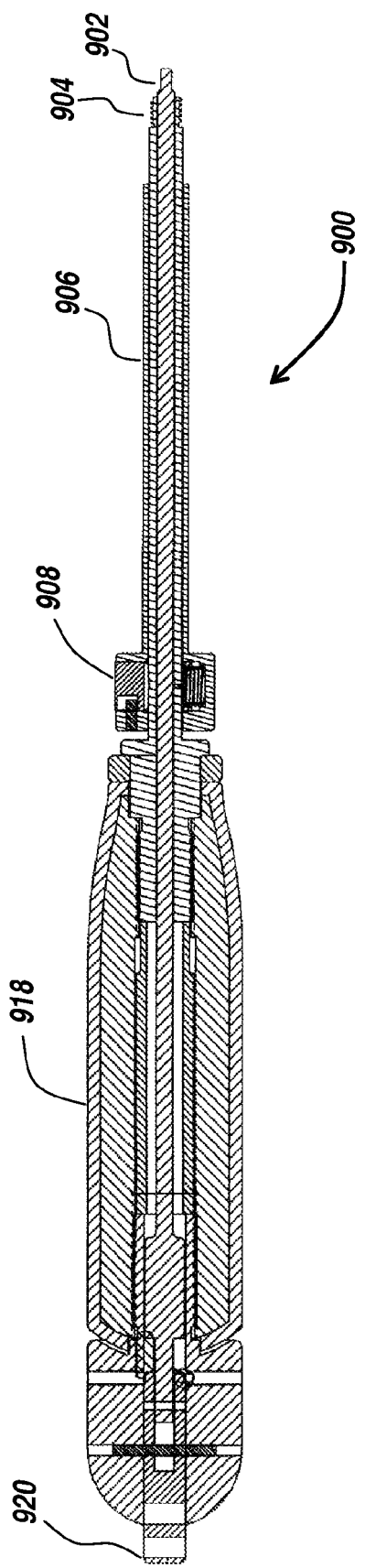
FIG. 9 is an assembled view of an alternate instrument for engaging an implantable polyaxial screw

FIG. 9 is a cutaway view of an embodiment of the present invention, wherein engagement of the drive feature 306 of the head 304 is accomplished using an moveable engagement mechanisms 902 that is actuated by a lever 920 arrangement. The present embodiment couples rotation of the engagement mechanism and the alignment mechanism together, such that rotation of the handle 918 results in rotation of both the engagement mechanism and the alignment mechanism.

In use the integral lever is operated to extend the engagement mechanism. Following extension of the engagement mechanism 902 the engagement mechanism may engage a drive feature 306 of a polyaxial screw shank 302. Additionally, rotation of the handle 918 allows for rotation of the integral alignment mechanism such that the alignment mechanism by rigidify the polyaxial screw assembly. A surgeon may then selectively drive the polyaxial screw in a variety of directions. Additionally, a counter-rotation mechanism capable of slideably moving along the length of the alignment mechanism may be employed to selectively orient the head of the polyaxial screw as needed by a surgeon. The exterior of the counter-rotation mechanism may have a variety of indicators for use in properly orientating the counter-rotation mechanism as required by an surgeon such that the benefits of a favored angle polyaxial screw can be exploited.

Figure 10:
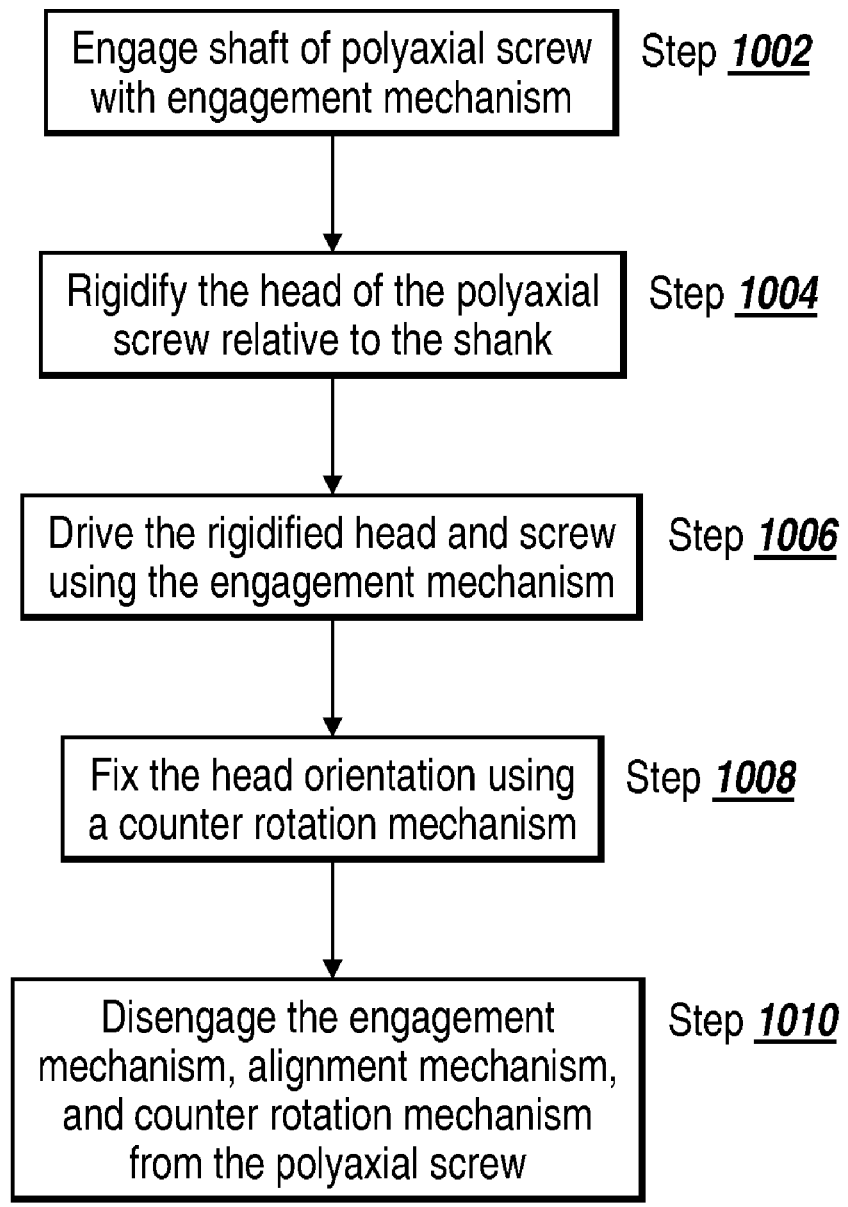
FIG. 10 is a flow chart illustrating the steps involved in implanting a polyaxial screw using the instrument of FIGS. 1-9.

FIG. 10 is a flowchart illustrating the steps necessary in practicing the present invention. In accordance with step 1002, the shaft portion of a polyaxial screw is first engaged by an engagement mechanism. Following engagement of the shank portion, the head portion is rigidified relative to the shaft portion using a alignment mechanism associated with the engagement mechanism. (step 1004) The rigidified head and shank of the polyaxial screw may be driven by a surgeon in accordance with step 1006 as required for the surgical procedure. The driving of the rigidified head and shank arrangement may be in a forward or reverse direction thereby allowing insertion of removal of the polyaxial screw assembly. Additionally, the orientation of the head portion of the polyaxial screw may be accomplished using a counter-rotation mechanism (step 1008) Proper orientation of the polyaxial screw head is beneficial when using a favored angle polyaxial screw. Orientation of the head may be accomplishing using a variety of means, including but not limited to the use of a indicating mechanism associated with the counter-rotation mechanism which provides a visual indicator of polyaxial screw head position. Upon proper orientation the engagement mechanisms, alignment mechanism and counter-rotation mechanism may be selectively disengaged from the polyaxial screw such that the driver may be removed from the implantable device (step 1010).

Figure 11A:
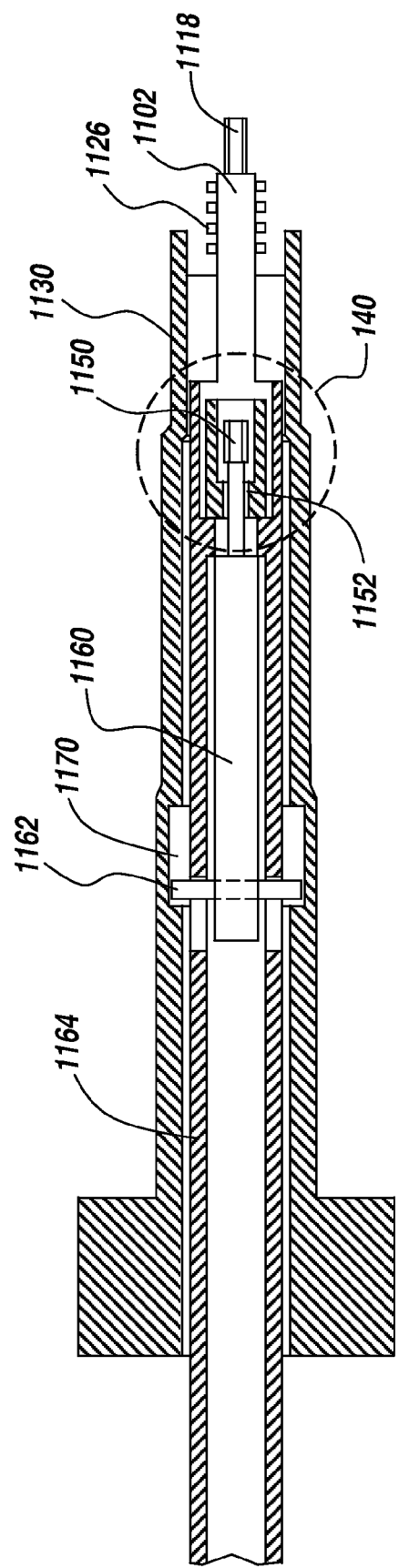
FIG. 11A is an embodiment of a the present invention in a disengaged state according to a first aspect.
Figure 11B:
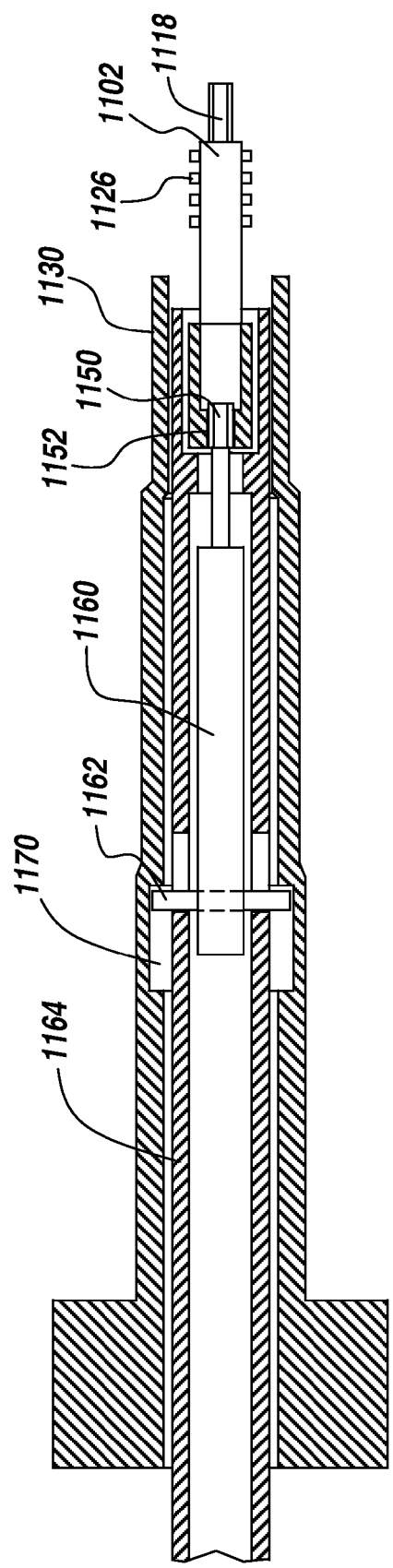
FIG. 11B is an embodiment of a the present invention in an engaged state according to a first aspect.

FIG. 11 is an embodiment of an alternate aspect of the present invention. As illustrated in FIGS. 11A and 11B, a moveable engagement mechanism 1102 is defined, wherein this moveable engagement mechanism 1102 has a hex tip 1118 for engaging a recess 306 in a polyaxial screw. As illustrated in the present embodiment, this moveable engagement mechanism 1102 is free to rotate in an unimpeded manner relative to a shaft 1164 when in a disengaged state (FIG. 11A) and is in a coupled state relative to the shaft 1164 (FIG. 11B) when properly engaged.

Engagement of the moveable engagement mechanism 1102 is accomplished using a male splined element 1150 and a female splined region 1152, wherein the male splined element is sized to engage the female splined region 1152 upon application of an external force. One skilled in the art will recognize that the use of a splined mating assembly is solely for illustrative purposes, and may be readily replaced by a suitable engagement mechanism as understood by a skilled practitioner. In the present embodiment of FIG. 11A, the male splined element 1150 and the female splined region 1152 is in a relieved position 1140, wherein the moveable engagement mechanism 1102 is not coupled to the instrument shaft 1162. In such an arrangement rotary motion delivered to the instrument shaft 1162 will not be translated to the moveable engagement mechanism 1102.

Should a surgeon elect to deliver rotary motion provided to a instrument shaft 1164 to the integral assembly 1102, the male splined element 1150 must first engage the female splined region 1152. Engagement is accomplished by slideably moving the counter-rotation sleeve 1130 in a rearward direction (i.e. away from the integral assembly and toward a handle (not shown)) A rearward motion results in the movement of the counter-rotation sleeve engagement region 1170, which is disposed within the counter-rotation sleeve 1130, in a rearward direction. After an appropriate displacement rearward, the counter-rotation sleeve engagement region 1170 will contact the actuator protrusion 1162 of an actuator assembly 1160. Further rearward displacement will in turn move the actuator 1160 in a similar rearward direction. Rearward motion of the actuator 1160 in turns causes subsequent engagement of the male splined element 1150, in communication with the actuator 1160, with the female splined region 1152 of the moveable engagement mechanism 1102. Following engagement of the male splined element 1150 with the female splined region 1152 the moveable engagement mechanism 1102 is now rigidly coupled to the shaft 1164. Rotational energy provided to the shaft 1164 is herein translated to the moveable engagement mechanism 1102. One skilled in the art will recognize that numerous engagement mechanism may be employed to couple the moveable engagement mechanism 1102 to the shaft 1164. An embodiment wherein the moveable engagement mechanism 1102 is coupled to the shaft 1164 is illustrated in FIG. 11B.

Figure 12:
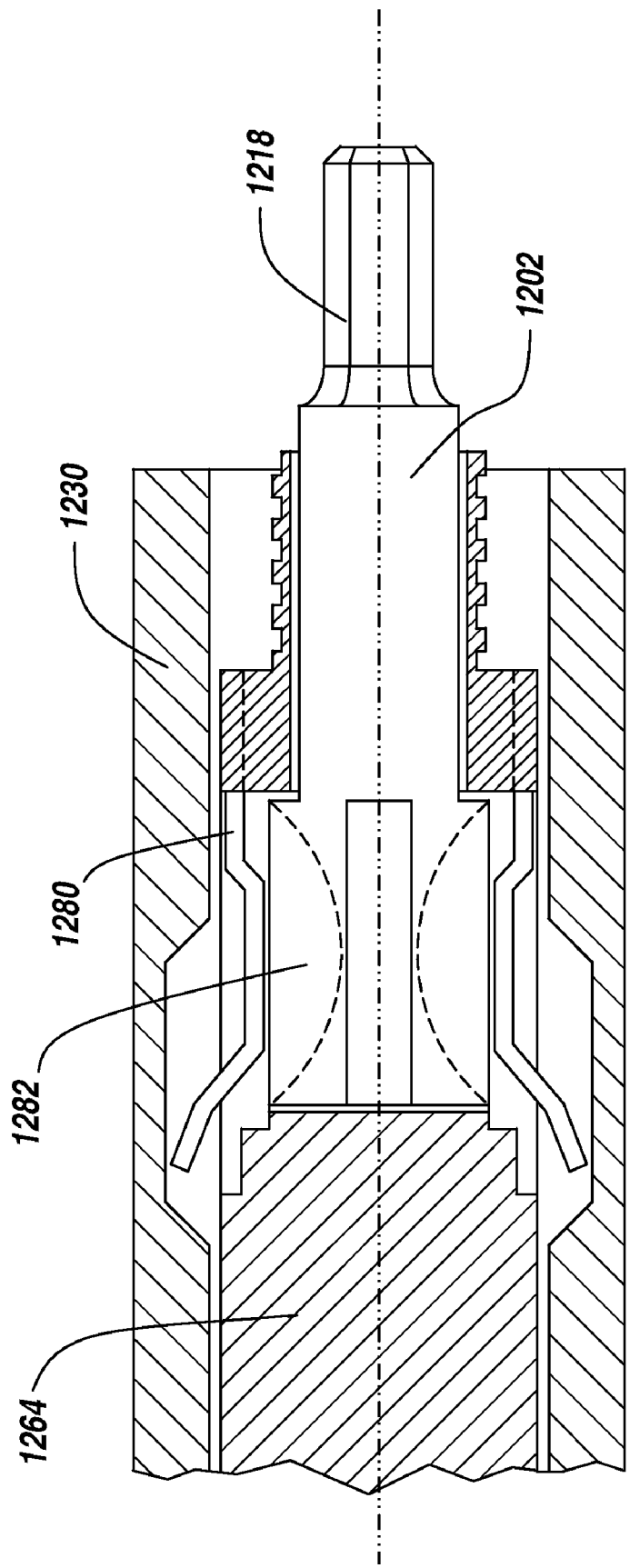
FIG. 12 is an embodiment of the present invention according to a second aspect.

An alternate embodiment illustrating the engagement of a moveable engagement mechanism 1202, having a hex tip 1218 disposed at its end, is illustrated in FIG. 12. Following displacement of the counter-rotation sleeve 1230 in a rearward direction the engagement tab 1280 is displaced to engage a annular recess 1282 of the moveable engagement mechanism 1202, thereby coupling the moveable engagement mechanism 1202 to the shaft 1264. One skilled in the art will recognize that the illustrated coupling embodiments are solely for illustrative purposes and are not intended to be limiting in scope.

Figure 13:
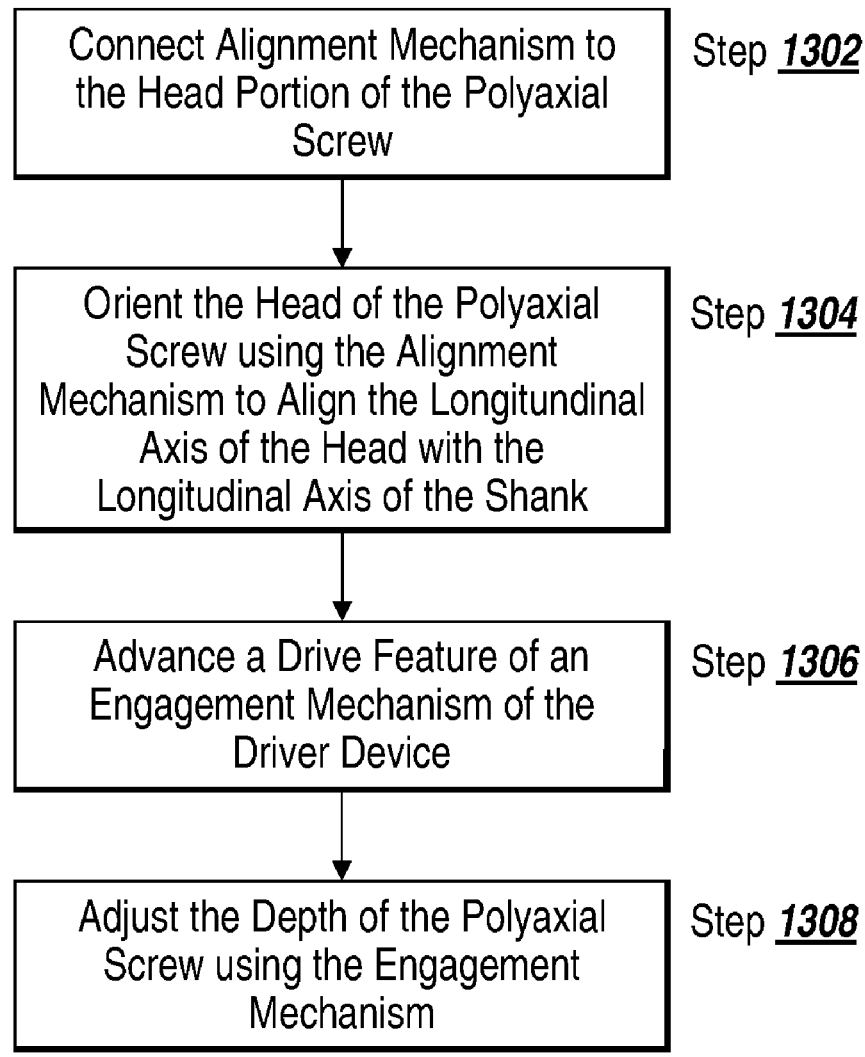
FIG. 13 is a flow chart illustrating the steps involved in adjusting a polyaxial screw using the instrument of FIGS. 1-9.

The present invention furthermore provides various methods for the insertion and adjustment of a polyaxial screw during surgery. As illustrated in the flowchart of FIG. 13, a polyaxial screw that has been implanted in vertebrae may be adjusted by a surgeon. In adjusting this screw an alignment mechanism of a driver device is connected to the head portion of a polyaxial screw implanted in a vertebra. (step 1302) The head is then orientated using the alignment mechanism to align the longitudinal axis of the head with the longitudinal axis of the shank of the polyaxial screw in accordance with step 1304. A drive feature of an engagement mechanisms is then advances (1306) such that the depth of the implanted polyaxial screw may be adjusted using this engagement mechanism. (step 1308)

Figure 14:
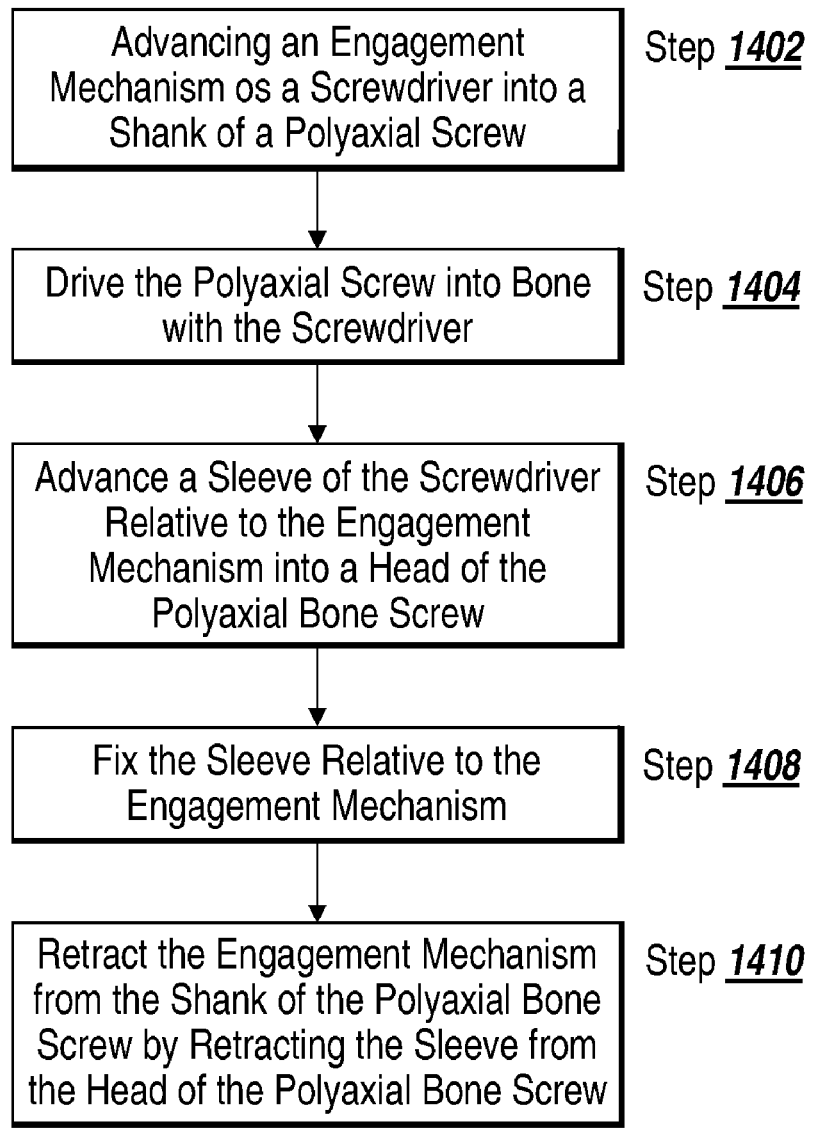
FIG. 14 is a flow chart illustrating the steps involved in removing a screwdriver from a polyaxial bone screw.

In accordance with FIG. 14, a polyaxial bone screw may further be removed from a screwdriver used in driving this screw. Removal occurs by first advancing an engagement mechanism into the shank of a polyaxial screw (step 1402) such that the engagement mechanism is capable of providing rotational energy to the shank of the polyaxial screw. The polyaxial screw is then driven into the region of bone (step 1404) as required by a surgeon. A sleeve may then be advanced wherein this sleeve moves relative to the engagement mechanism to engage the head of the polyaxial bone screw (step 1406). The sleeve is then fixed in location relative to the engagement mechanism in accordance with step 1408) and then the engagement mechanism may be retracted from the shank of the polyaxial screw by retracting the sleeve from the head of the polyaxial bone screw (step 1410).

Figure 15:
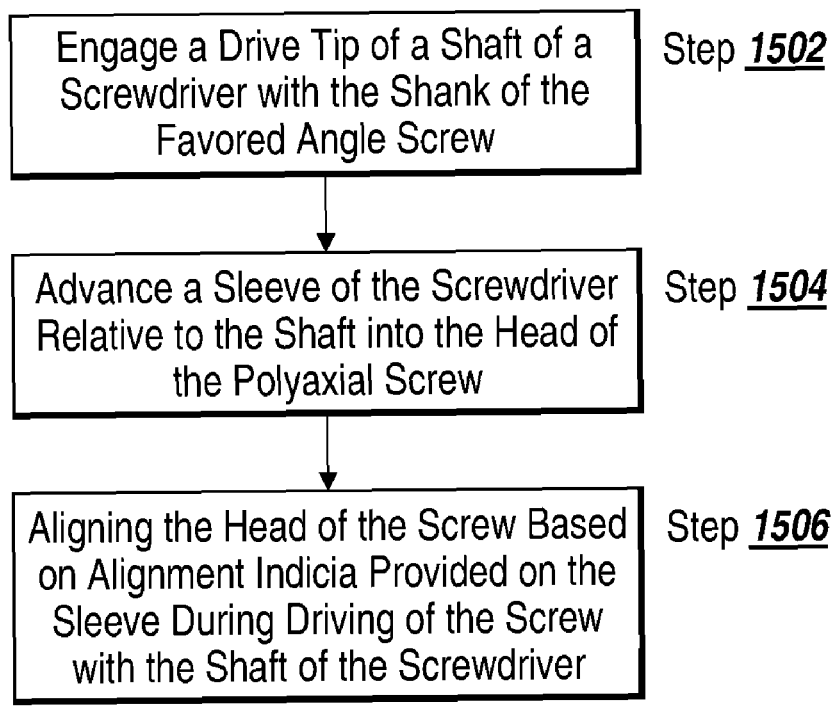
FIG. 15 is a flow chart illustrating the steps involved in inserting a favored angle polyaxial screw.

In accordance with an embodiment of the present invention a method for inserting a favored angle polyaxial screw is recited. This method is represented by the flowchart of FIG. 15. In accordance with this method a drive tip of a shaft of a screwdriver is engaged with the shank of a favored angle screw (step 1502). A sleeve is then advanced relative to the shaft such that the sleeve is coupled to the head of the polyaxial screw (step 1504). In accordance with step 1506 the head of the screw is aligned using an alignment indicator provided on the sleeve during the driving of the polyaxial screw with the shaft of the screwdriver.

Figure 16:
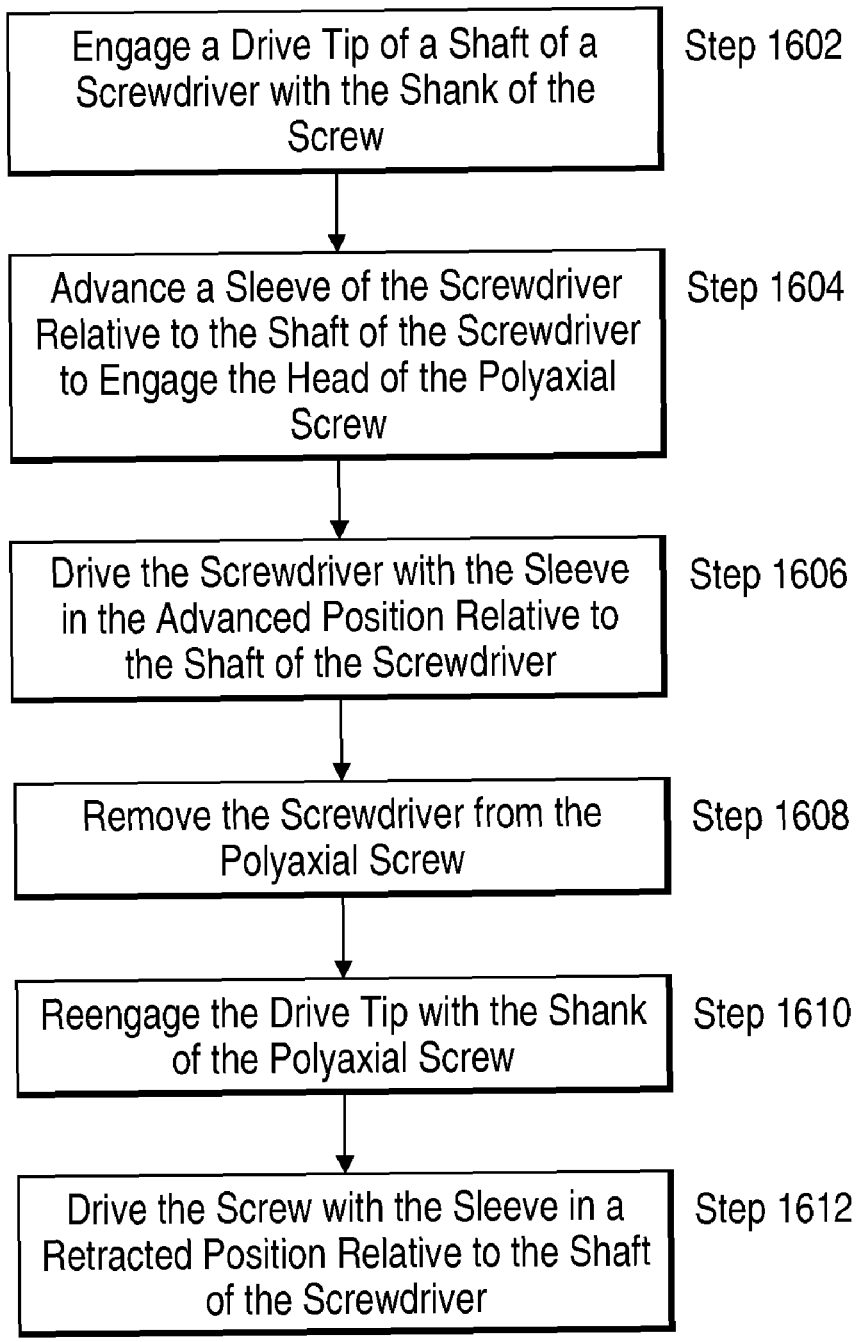
FIG. 16 is a flow chart illustrating the steps involved in implanting a polyaxial screw using the instrument of FIGS. 1-9.

In accordance with FIG. 16, a method for implanting a polyaxial screw having a head and a shank is provided. A drive tip of a shaft of a screwdriver is engaged with the shank of a polyaxial screw (step 1602) and a sleeve is advanced in a direction relative to the longitudinal axis of the shaft of the screwdriver such that the head of the polyaxial screw is engaged (step 1604). The screwdriver is then driven with the sleeve in an advanced position relative to the shaft of the screwdriver in accordance with step 1606. The screwdriver is then removed from the polyaxial screw (step 1608). The drive tip may then reengage the shank of the polyaxial screw (step 1610) such that the polyaxial screw can be driven with the sleeve in a retracted position relative to the shaft of the screwdriver (step 1612)

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the instrument of the illustrative embodiment of the invention is not limited to use with polyaxial screws and can be used with any suitable implant for any suitable orthopedic system.

It is also to be understood that the following claims are to cover all generic and specific features of the invention described herein, and all statements of the scope of the invention which, as a matter of language, might be said to fall therebetween.

The invention claimed is:

1. A system comprising an implantable device and an instrument for manipulating the implantable device, the instrument comprising:

an engagement mechanism extending along an axis and selectively engaging a first portion of the implantable device, an alignment mechanism disposed on an exterior surface of the engagement mechanism, moveable relative to the engagement mechanism, and selectively engaging a second portion of the implantable device to align the second portion of the implantable device with the first portion of the implantable device, and a plurality of stops formed on the exterior surface of the engagement mechanism for defining multiple positions of the alignment mechanism on the exterior surface of the engagement mechanism, wherein the alignment mechanism includes a component to selectively engage the plurality of stops such that an engagement of the alignment mechanism with each of the plurality of stops prevents the alignment mechanism from moving along the axis of the engagement mechanism, the alignment mechanism rotating around the axis of the engagement mechanism at the positions where the alignment mechanism engages the plurality of stops;

a counter-rotation mechanism disposed on an exterior surface of the alignment mechanism and rotating independently of the engagement mechanism and the alignment mechanism to selectively orientate the second portion of the implantable device relative to the first portion of the implantable device during operation of the implantable device, wherein the implantable device is inserted, adjusted and removed with the instrument.

2. The system of claim 1 further comprising a handle assembly, said handle assembly sized and oriented to provide rotational energy to the instrument for operating an implantable device.

3. The instrument of claim 1, wherein the first portion of the implantable device is the shank of a polyaxial screw.

4. The instrument of claim 1, wherein the second portion of the implantable device is the head of a polyaxial screw.

5. The system of claim 1, wherein said alignment mechanism is selectively engageable to or disengageable from the implantable device.

6. The system of claim 5, wherein said alignment mechanism has a threaded tip portion for engagement with the second portion of the implantable device.

7. The system of claim 5, wherein the alignment mechanism is engageable to the implantable device for rigidifying the implantable device.

8. The system of claim 1, wherein the plurality of stops comprise a first and second stop, said first and second stop defining an extended and retracted position of said alignment mechanism.

9. The system of claim 1, wherein the counter-rotation mechanism further comprises an engageable protrusion, sized for mating with a corresponding feature of the implantable device, to orientate the second portion of the implantable device.

10. The system of claim 1, wherein the counter-rotation mechanism further comprises a collar, said collar allowing orientation of the second portion of the implantable device.

11. The system of claim 1, wherein the engageable mechanism further comprises a hex head for engaging a first portion of the implantable device.

12. A system comprising a polyaxial screw having a head portion moveable relative to a shaft portion, and a driver device for the polyaxial screw, the driver device comprising:

an engagement mechanism defining a first axis, said engagement mechanism sized for engaging the shaft portion of the polyaxial screw, an alignment mechanism disposed on an exterior surface of the engagement mechanism and orientated along the first axis, said alignment mechanism capable of engaging the head portion of the polyaxial screw and rigidifying the head portion relative to the shaft portion of the polyaxial screw, a plurality of stops formed on the exterior surface of the engagement mechanism for defining multiple positions of the alignment mechanism on the exterior surface of the engagement mechanism, wherein the alignment mechanism includes a component to selectively engage the plurality of stops such that an engagement of the alignment mechanism with each of the plurality of stops prevents the alignment mechanism from moving along the first axis of the engagement mechanism, the alignment mechanism rotating around the first axis at the positions where the alignment mechanism engages the plurality of stops, and a counter-rotation mechanism disposed on an exterior surface of the alignment mechanism and orientated along the first axis and selectively orientating the head portion of the polyaxial screw relative to the shaft portion of the polyaxial screw, wherein the engagement mechanism, the alignment mechanism and the counter-rotation mechanism rotate along the first axis independently of each other, wherein the polyaxial screw is inserted, adjusted and removed with the driver.

13. The system of claim 12, wherein the engagement mechanism further comprises a hex shaped tip for engaging the shaft portion of the polyaxial screw.

14. The system of claim 12, wherein the alignment mechanism has a threaded region which engages the inner region of the head portion of the polyaxial screw.

15. The driver device of claim 12, wherein the counter-rotation mechanism further comprises an indicating mechanism associated with the counter-rotation mechanism for displaying the orientation of the head portion of the polyaxial screw.

16. The system of claim 12, wherein the plurality of stops define an extended alignment mechanism position and a retracted alignment mechanism position.

17. A system comprising an implantable polyaxial screw and an apparatus for operating the implantable polyaxial screw, the apparatus comprising:

an engagement shaft extending along an axis with a drive tip for selectively engaging a shaft of a polyaxial screw;

an alignment sleeve disposed on an exterior surface of the engagement shaft and moveable relative to the engagement shaft, wherein the distal end of the alignment sleeve selectively engages a head of a polyaxial screw;

a plurality of stops formed on the exterior surface of the engagement shaft for defining multiple positions of the alignment sleeve on the exterior surface of the engagement shaft, wherein the alignment sleeve includes a component to selectively engage the plurality of stops such that an engagement of the alignment sleeve with each of the plurality of stops prevents the alignment sleeve from moving along the axis of the engagement shaft, the alignment sleeve rotating around the axis of the engagement shaft at the positions where the alignment sleeve engages the plurality of stops; and a counter-rotation sleeve disposed on an exterior surface of the alignment sleeve and rotating independently of the alignment sleeve and the engagement shaft, wherein the distal end of the counter-rotation sleeve selectively orientates the head of the polyaxial screw relative to the shank of the polyaxial screw during operation of the polyaxial screw, wherein the polyaxial screw is inserted, adjusted and removed with the apparatus.

* * * * *